United States Patent [19]
Froehlich

[11] Patent Number: 5,865,173
[45] Date of Patent: Feb. 2, 1999

[54] BILEVEL CPAP SYSTEM WITH WAVEFORM CONTROL FOR BOTH IPAP AND EPAP

[75] Inventor: James P. Froehlich, Berlin, Pa.

[73] Assignee: Sunrise Medical HHG Inc., Longmont, Colo.

[21] Appl. No.: 554,595

[22] Filed: Nov. 6, 1995

[51] Int. Cl.[6] ............ A61M 16/00; A62B 7/04; F16K 31/02; F16K 31/26
[52] U.S. Cl. ............... 128/204.23; 128/204.21; 128/204.26
[58] Field of Search ............. 128/204.21, 204, 128/23, 204.26, 204.18, 204.22

[56] References Cited

U.S. PATENT DOCUMENTS

| | | | |
|---|---|---|---|
| 3,598,111 | 8/1971 | Kahn et al. | |
| 3,905,362 | 9/1975 | Eyrick et al. | 128/204.21 |
| 3,910,270 | 10/1975 | Stewart . | |
| 3,961,627 | 6/1976 | Ernst et al. | 128/204.21 |
| 3,991,304 | 11/1976 | Hillsman . | |
| 4,036,221 | 7/1977 | Hillsman et al. . | |
| 4,155,356 | 5/1979 | Venegas | 128/204.21 |
| 4,351,344 | 9/1982 | Stenzler . | |
| 4,393,869 | 7/1983 | Boyarsky et al. | 128/204.18 |
| 4,448,192 | 5/1984 | Stawicke et al. | 128/204.21 |
| 4,481,944 | 11/1984 | Bunnell | 128/204.18 |
| 4,538,604 | 9/1985 | Usry et al. | 128/204.23 |
| 5,092,326 | 3/1992 | Winn et al. | 128/205.13 |
| 5,107,830 | 4/1992 | Younes | 128/204.18 |
| 5,117,819 | 6/1992 | Servidio et al. | 128/204.18 |
| 5,134,995 | 8/1992 | Gruenke et al. | 128/204.23 |
| 5,148,802 | 9/1992 | Sanders et al. | 128/204.18 |
| 5,161,525 | 11/1992 | Kimm et al. | 128/204.26 |
| 5,199,424 | 4/1993 | Sullivan et al. | 128/204.18 |
| 5,239,995 | 8/1993 | Estes et al. | 128/204.23 |
| 5,313,937 | 5/1994 | Zdrojkowski | 128/202.22 |
| 5,433,193 | 7/1995 | Sanders et al. | 128/204.18 |
| 5,438,980 | 8/1995 | Phillips | 128/204.23 |
| 5,492,113 | 2/1996 | Estes et al. | 128/204.23 |
| 5,522,382 | 6/1996 | Sullivan et al. | 128/204.21 |
| 5,522,397 | 6/1996 | Vermaak | 128/532 |
| 5,535,738 | 7/1996 | Estes et al. | 128/204.21 |
| 5,555,880 | 9/1996 | Winter et al. | 128/204.21 |

*Primary Examiner*—Kimberly L. Asher
*Attorney, Agent, or Firm*—MacMillan, Sobanski & Todd, LLC

[57] ABSTRACT

A bilevel continuous positive airway pressure (CPAP) respiratory therapy system which applies a prescribed inspiratory positive airway pressure (IPAP) to a patient's respiratory system during inhalation and applies a lower prescribed expiratory positive airway pressure (EPAP) to the respiratory system during exhalation. A blower provides pressurized air at least at the IPAP pressure. A fast response vent valve reduces the pressure applied to the patient to the EPAP level during exhalation and increases the pressure to the set IPAP level during inhalation. Leading edges of pressure changes between the IPAP and EPAP levels are rounded by an adjustable amount to enhance patient comfort and/or to allow the physician to modify the therapy. In an alternate embodiment, the pressure is controlled by controlling the speed of the blower.

6 Claims, 3 Drawing Sheets

BILEVEL CPAP SYSTEM WITH WAVEFORM CONTROL FOR BOTH IPAP AND EPAP

TECHNICAL FIELD

The invention relates to continuous positive airway pressure (CPAP) respiratory therapy apparatus and more particularly to a bilevel CPAP system having control over the inspiratory and expiratory air pressure waveforms.

BACKGROUND ART

CPAP apparatus is well recognized for use in the treatment of a number of respiratory conditions such as, for example, obstructive sleep apnea and hypopnea. The apparatus applies a continuous positive pressure through a mask or a nasal cannula to a patient's respiratory system while the patient sleeps. The positive pressure acts as a pneumatic splint for expanding and preventing blockage of the upper airway. Typical CPAP apparatus includes a blower which produces pressurized air, a mask or nasal cannula and a hose connecting between the blower and the mask or cannula. The apparatus also includes a pressure controller. The CPAP pressure is measured either at the mask or at a base unit as delivered to the hose. The pressure is compared with a stored prescribed pressure and errors are used to adjust the pressure, typically by controlling the speed of the blower. The pressure controller also may be programmed to provide variations to the applied pressure, generally either based on time or based on patient need. The applied pressure has been controlled to provide an initial low positive pressure to make the patient more comfortable while falling asleep. As the patient falls asleep, the pressure is ramped up to the prescribed pressure either over a set period of time or after a set low pressure delay time. It also is known that the patient's breathing may be monitored and that the pressure may be automatically adjusted to increase the applied pressure in response to the detection of apnea and/or precursors to apnea, such as snoring, and to gradually decrease the applied pressure in response to the absence of apnea and/or snoring. Apparatus of this type automatically adjusts to the lowest pressure necessary to maintain airway patency.

More advanced CPAP systems provide two air pressure levels to the patient's respiratory system, namely, an inspiratory positive airway pressure (IPAP) during inhalation and a lower expiratory positive airway pressure (EPAP) during exhalation. For most patients requiring CPAP therapy, a higher IPAP pressure is required to maintain airway patency during inhalation, and a much lower EPAP pressure is sufficient to maintain airway patency during exhalation. Often, the EPAP pressure may be at or only slightly above ambient pressure, while the IPAP pressure is generally set to a pressure greater than the EPAP setting to provide the therapy needed during inspiration. By providing bilevel operation with the lowest necessary EPAP pressure, the work required for the patient to exhale is reduced and therefore the patient's comfort is increased. This in turn promotes patient compliance with the prescribed therapy.

Bilevel CPAP systems typically use one of two methods for controlling pressure. In both systems, a breathing signal is established to determine when the patient inhales and exhales. While the patient inhales, the applied pressure is set to the prescribed IPAP level and, when the patient exhales, the applied pressure is set to the prescribed EPAP level. When a person breathes, there is a slight pause between inspiration and expiration. In some systems, the EPAP and IPAP levels are changed in response to the beginnings of inspiration and expiration and in others the EPAP and IPAP levels are changes in response to the beginnings of the pauses. Some systems modulate the speed of the blower to increase and decrease the applied pressure. In other systems, the blower is set to provide a pressure of at least as high as the higher IPAP level and a vent valve is modulated to reduce the pressure to the prescribed levels during inspiration and expiration. When the blower speed is modulated, the pressure quickly ramps up to the prescribed IPAP pressure when inhalation begins and quickly ramps down to the prescribed EPAP pressure when exhalation begins. There is a slight ramping effect when the pressure is changed due to the inertia of the blower when changing blower speeds. When a vent valve is modulated, there may be a more abrupt change between the IPAP and EPAP levels, resulting in a square wave shape to the applied pressure. In both types of systems, the waveform will tend to have a slight pressure dip at the onset of inhalation followed by a sudden increase in pressure as the level increases towards the desired IPAP level. A short duration pressure spike typically is present during the onset of exhalation followed by a sudden decrease in pressure as the level decreases towards the desired EPAP level.

In the past, each commercially available bilevel CPAP system has had a particular profile to the applied pressure waveform based on the particular response of the blower and/or vent valve and the related control circuitry. The waveform has not been adjustable to enhance the comfort of the patient or to allow the physician to modify the therapy. The only waveform control available to the physician or therapist is to set the prescribed IPAP and EPAP pressures.

DISCLOSURE OF INVENTION

According to the invention, a bilevel CPAP system is provided with a control over the waveform of the applied pressure to allow the physician to adapt the system to the needs of a specific patient. The waveform may be set, for example, to maximize patient comfort or to modify the therapy. The CPAP system includes a blower, a vent valve and a controller mounted in a base unit and connected through a hose to either a mask or a nasal cannula for applying a positive air pressure to a patient's respiratory system. The applied pressure and/or the air flow to the patient is monitored and a breathing signal is established to indicate when the pressure should be increased to the IPAP level and decreased to the EPAP level. The levels may be changed at or about the time of the beginnings of inspiration and expiration. In response to the breathing signal and the set IPAP and EPAP levels, a generally square wave signal is produced for operating the vent valve to quickly change between the IPAP and EPAP levels. According to the invention, each leading edge of the square wave which increases the pressure to the set IPAP level is rounded and each leading edge of the square wave which decreases the pressure to the set EPAP level is rounded. The degree of rounding is separately set for the IPAP and EPAP levels. The effect of the rounding is to lessen the suddenness of the pressure changes on the patient. The patient also may be able to handle a higher IPAP pressure if the transition is more subtle than a square wave or a trapezoidal wave. This in turn can increase patient comfort. However, the leading edges of the wave cannot be rounded to the point that the set therapeutic pressures are not achieved. By providing a selectable rounding factor, the physician may set the degree of waveform rounding to meet the needs of a particular patient.

Accordingly, it is an object of the invention to provide a bilevel CPAP system having a control for modifying the shape of the applied pressure waveform as it changes between IPAP and EPAP levels.

Other objects and advantages of the invention will become apparent from the following detailed description of the invention and the accompanying drawings.

BEST MODE FOR CARRYING OUT THE INVENTION

Figure 1:
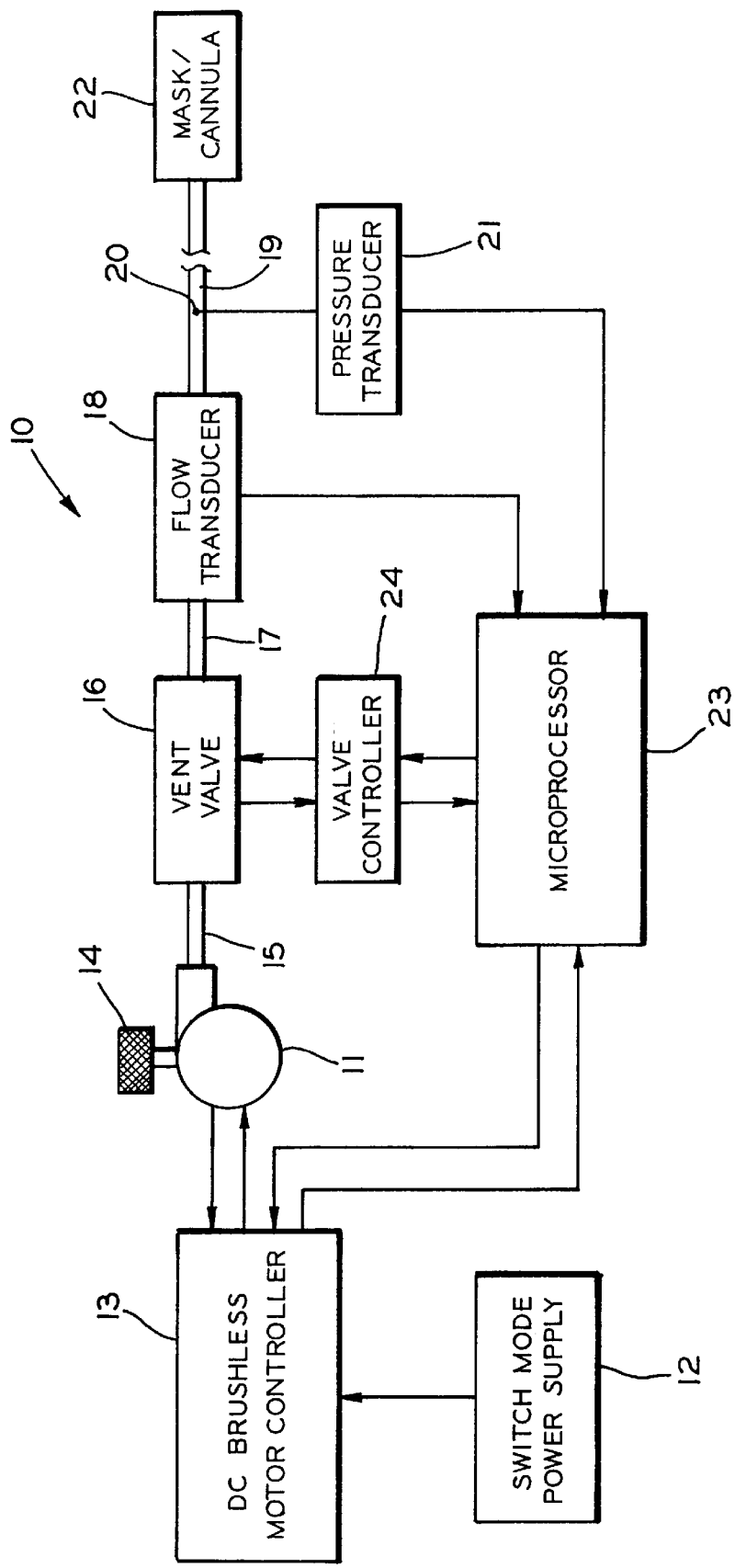
FIG. 1 is a schematic block diagram of bilevel CPAP apparatus according to a preferred embodiment of the invention.

Referring now to FIG. 1 of the drawings, a block diagram is shown for CPAP apparatus 10 according to the invention. The apparatus 10 includes a blower 11 for establishing a predetermined pressurized flow of air. Preferably, the blower 11 has a DC brushless electric motor. The blower 11 is operated from a commercially available switchmode power supply 12 and a DC brushless motor controller 13. The blower 11 receives ambient air from an intake filter 14 and delivers the air through a conduit 15 to a vent valve 16. From the valve 16, the pressurized air flows through a conduit 17 to a mass air flow transducer 18 and then is delivered to a long flexible tube 19. A tap 20 located in the tube 19 adjacent the flow transducer 18 is connected to a pressure transducer 21 for detecting the pressure of the air delivered through the tube 19 to the patient. A remote end of the tube 19 is connected through either a mask or a nasal cannula 22 to deliver the pressurized air to the patient's respiratory system. In response to information from the flow transducer 18 and the pressure transducer 21 and to stored data, a microprocessor 23 controls the speed of the blower 11 and also provides information to a valve controller 24 which controls the vent valve 16 to control the air pressure applied to the patient.

In operation, the desired IPAP and EPAP pressures are stored in the microprocessor 23 by the physician or by a technician based upon a prescription from a physician or from a respiratory therapist. When the apparatus 10 is turned on, the microprocessor 23 supplies a signal to the motor controller 13 to set the blower motor speed to a level for establishing at least the prescribed IPAP pressure to the mask or cannula 22 when the vent valve 16 is closed and the mask or cannula 22 is connected to the patient.

From data received from the flow transducer 18 and from the pressure transducer 21, the microprocessor 23 can determine the air pressure at the mask or cannula 22, the air flow in the patient's respiratory system as the patient inhales and exhales and any leakages in the system. It will be appreciated that the pressure at the tap 20, which is located in a base unit including the blower 11, the vent valve 16, the microprocessor 23 and the related transducers 18 and 21 and controllers 13 and 24, will increase and decrease as the patient exhales and inhales, respectively. The air flow, as measured by the mass flow transducer 18, also will vary with inhalation and exhalation and with air leakages such as between the mask or cannula 22 and the patient. There will be a pressure drop in the tube 19 based upon its length, diameter and on the flow resistance of its interior surface. This pressure drop is a function of the air flow rate through the tube. From the measured air flow, the pressure drop in the tube 19 can be calculated or looked up in a table and is subtracted from the pressure measured by the transducer 21 to determine the pressure at the mask or cannula 22.

The flow measured by the flow transducer 18 will be cyclic about an average value. During inhalation, the flow will increase above the average and during exhalation, the flow will decrease below the average. The average value, which corresponds to the air flow when the patient pauses between inhalation and exhalation, represents air leakage in the system. If the average flow is deducted from the indicated flow, the resulting air flow curve represents the actual air flow in the patient's respiratory system.

The pressurized air flow, as measured by the flow transducer 18, also may be used by the microprocessor 23 to generate a patient breathing signal. The breathing signal may be a square wave signal which has one voltage or logic level when the patient inhales and a different voltage or logic level when the patient exhales. The generation of the breathing signal is not a part of this invention. Exemplary apparatus for generating a square wave breathing signal is described, for example, in U.S. patent application Ser. No. 08/356,471 entitled Control For CPAP Apparatus, the disclosure of which is incorporated herein. An alternate method for generating a patient breathing signal is illustrated in U.S. Pat. No. 5,433,193 entitled Breathing Gas Delivery Method And Apparatus. Here, the instantaneous air flow rate is continuously compared with the average flow rate. The breathing signal is set to the inhalation level whenever the instantaneous air flow rate exceeds an average flow rate and is set to an expiration level whenever the instantaneous air flow rate falls below the average flow rate. It also is known that a breathing signal may be established in response to changes in the slope of the instantaneous air flow rate.

Figure 2:
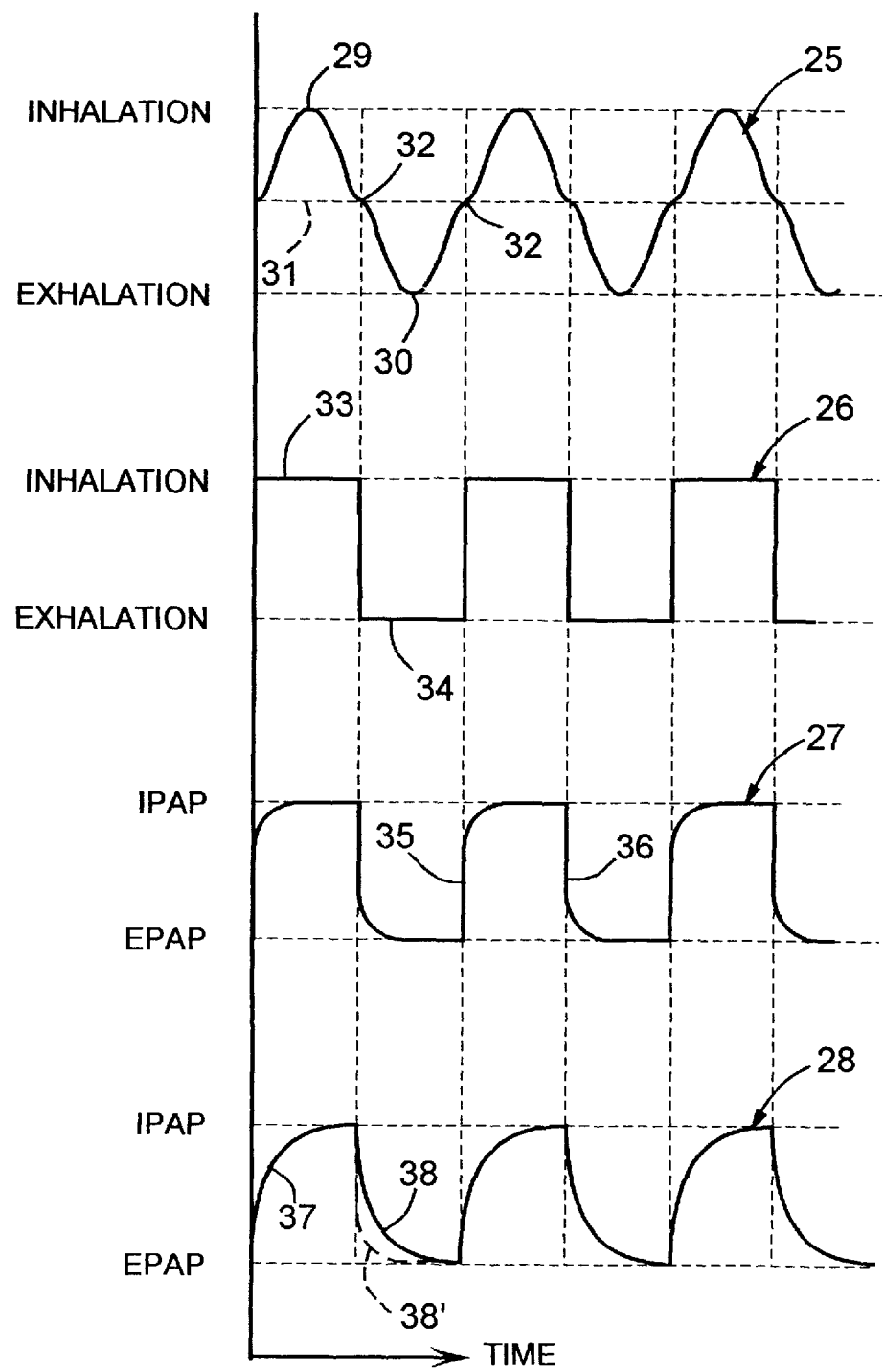
FIGS. 2 is a graph showing exemplary waveforms of CPAP air flow to the patient, of a breathing signal and of the applied CPAP pressure with two different inspiratory and expiratory rounding factors.

FIG. 2 is a graph showing an exemplary curve 25 of air flow to a patient's respiratory system during spontaneous breathing, a curve 26 illustrating a typical square wave breathing signal, a CPAP pressure curve 27 with a small amount of leading edge rounding and a CPAP pressure curve 28 with a larger amount of leading edge rounding. The air flow curve 25 has a generally sinusoidal shape, alternating between inhalation peak flow at 29 and exhalation peak flow at 30. A dashed line 31 represents no air flow in the respiratory system and corresponds to air leakage at the patient. There typically are slight pauses 32 near or on the line 31 at the end of each inhalation phase and at the end of each exhalation phase. The breathing signal curve 26 is a square wave which alternates between a first logic level 33 during inhalation and a second logic level 34 during exhalation. It will be appreciated that although the first logic level 33 is shown as high and the second logic level is shown as low, the levels may be inverted. It also should be appreciated that the leading edges of the breathing signal curve 26 may be synchronized with various portions of the air flow curve 25, such as when the curve 25 crosses the line 31, or at the beginning of the pauses 32 between inhalation and exhalation, or shortly prior to the endings of inhalation and exhalation.

The microprocessor 23 (FIG. 1) applies a signal to the valve controller 24 for operating the vent valve 16 to establish the prescribed IPAP pressure during inhalation and the prescribed EPAP pressure during exhalation. According to the prior art, the vent valve 16 would be operated to produce a substantially square wave pressure waveform which corresponds in shape and in synchronism with the square wave breathing signal curve 26. According to the invention, the vent valve 26 is selected to have a very rapid response which corresponds to a valve control signal from the microprocessor. The valve control signal from the microprocessor 23 is applied to the valve controller 24 which includes a pulse width modulator for producing a voltage which operates the valve 16. The control voltage is modified from the square wave breathing signal curve 26 to produce a curve having rounded or shaped leading edges when changing the pressure level from the EPAP level to the IPAP level when inhalation begins and from the IPAP level to the EPAP level when exhalation begins. The degree of rounding is individually selected for the both the leading edge of the EPAP level and the leading edge of the IPAP level. Thus, the rapid response vent value 16 in combination with the programmed microprocessor 23 which controls operation of the vent valve 16 form a means for modifying of changing the profile of leading edges of the applied pressure waveform as such waveform alternately changes between EPAP and IPAP levels. The microprocessor 23 controls the opening and closing of the vent valve 16 to impart the desired leading edges profiles to the EPAP and IPAP waveforms. The microprocessor 23 is programmed to permit changing the leading edges profiles.

The curve 27 in FIG. 2 illustrates the pressure applied to the patient with minimal edge rounding both on rising portions 35 of the curve 27 when inhalation begins and on falling portions 36 of the curve when exhalation begins. The curve 28 illustrates the pressure applied to the patient with maximum edge rounding both for rising portions 37 of the curve 28 when inhalation begins and for falling portions 38 of the curve 28 when exhalation begins. However, the rounding may be set separately for the rising portions 35, 37 and for the falling portions 36, 38 of the curves 27 and 28. For example, the curve 28 may be modified so that the pressure curve 37 is highly rounded when inspiration begins and the pressure follows a curve portion 38' which has minimally rounding when exhalation begins.

Figure 3:
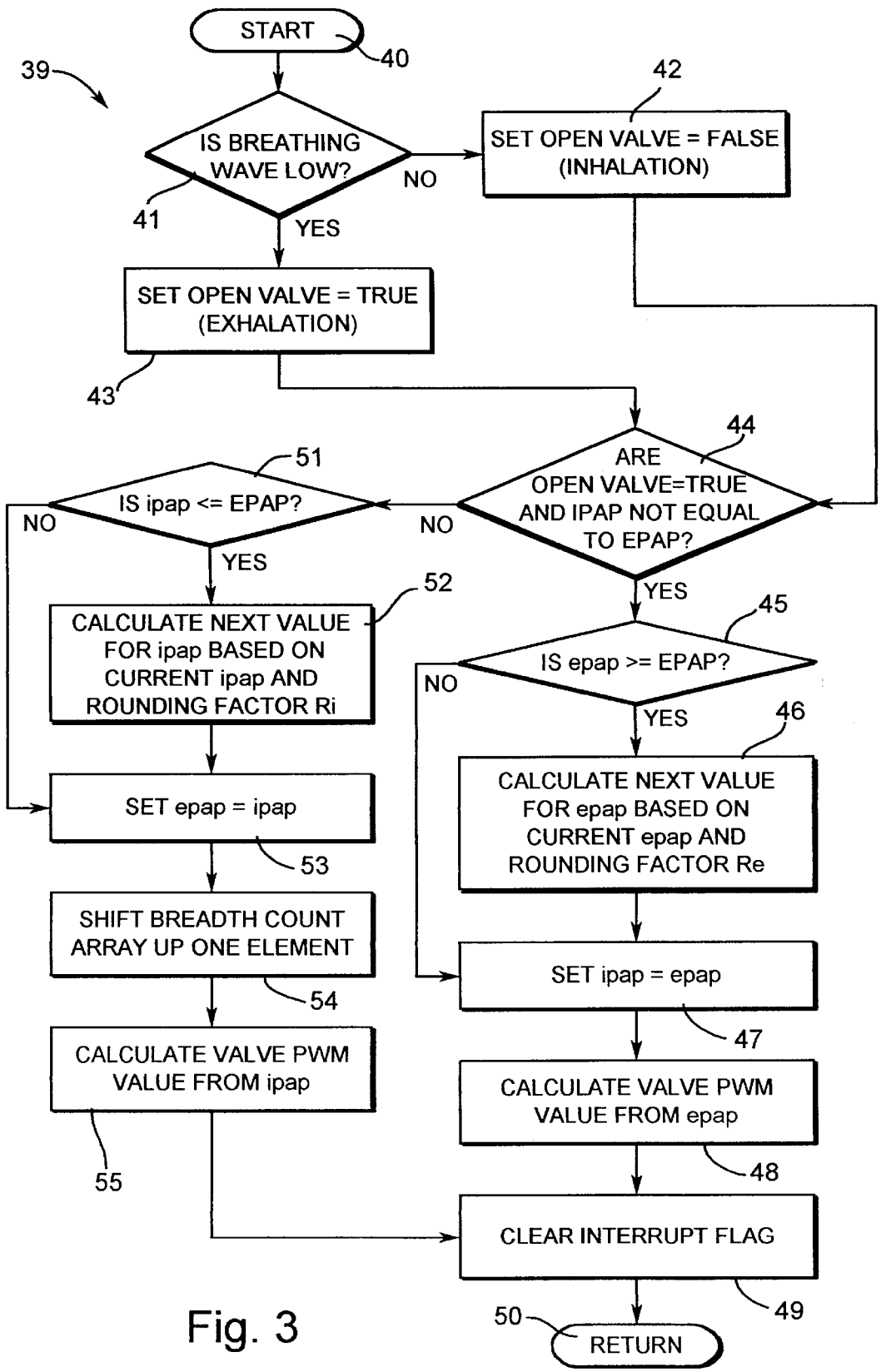
FIG. 3 is a flow chart showing operation of the controller for adjusting the shape of the air pressure waveform.

FIG. 3 is a flow diagram 39 illustrating the process used by the microprocessor 23 (FIG. 1) for rounding the leading edges of the pressure curve when it alternately changes between the EPAP and IPAP levels. In reading the flow chart 39, the capital letters "EPAP" and "IPAP" represent the prescribed EPAP and IPAP levels which are stored in the memory of the microprocessor 23. The lower case letters "epap" and "ipap" represent the current or instantaneous values for the pressures as calculated and set by the microprocessor 23. The flow diagram 39 is initially entered at a terminal 40. Transitions of the breathing square wave signal cause entry at the start terminal 40. The transitions may be detected by polling the status of the breathing signal or by a software interrupt. At a decision block 41 it is determined if the breathing wave 34 is low to indicate exhalation or high to indicate inhalation. If the patient is inhaling, an open valve flag is set false at a block 42 and if the patient is exhaling the open valve flag is set true at a block 43. In either event, a decision block 44 next determines if both the open valve flag is true and the prescribed IPAP level does not equal the prescribed EPAP level. The prescribed IPAP and EPAP levels will be equal only if the apparatus 10 is set to provide a constant pressure to the patient, i.e., there is no pressure change between inhalation and exhalation.

If the patient breathing curve 26 shows that the patient is exhaling and the apparatus 10 is in a bilevel operating mode, the program asks at a decision block 45 if the current EPAP level is greater than or equal to the prescribed EPAP level. If so, a new current EPAP level is calculated at a block 46 from the current EPAP level, the prescribed EPAP level and an expiration rounding factor Re and the program proceeds to a block 47. If the current EPAP level was not greater than or equal to the prescribed EPAP level at the block 45, the program skips the block 46 and jumps directly to the block 47. At the block 47, the value stored as the current IPAP level is set to the value of the current EPAP level so that there is no sudden change in the setting of the valve 16 when exhalation ends and inhalation begins. A valve pulse width modulation value is then calculated at a block 48 for operating the valve controller 24 (FIG. 1), an interrupt flag is cleared at a block 49 and the flow chart loop 39 returns to the main program in the microprocessor 23 at a terminal 50. The main operating program is set to cycle through the program loop illustrated by the flow diagram 39 at a set clock frequency, such as at a rate of 16 Hz.

If either the apparatus 10 is not operating in a bilevel mode or the breathing signal 26 is at the inhalation level 33, the program moves from the block 44 to a decision block 51 and asks if the current IPAP level is less than or equal to the prescribed IPAP level. If so, a new IPAP level is calculated at a block 52 based on the current IPAP level, the prescribed IPAP level and a stored inhalation rounding factor Ri. The program then proceeds either from the block 52 or from the block 51 to a block 53 where the value stored as the current EPAP level is set to the value of the current IPAP level so that there is no sudden change in the setting of the valve 16 when inhalation ends and exhalation begins. Optionally, a breath count maintained in the microprocessor 23 may be incremented at a block 54. A valve pulse width modulation value is then calculated at a block 55 from the calculated current IPAP value and the program proceeds through the block 49, where an interrupt flag is cleared, to the program return terminal 50.

At the block 46, the microprocessor 23 calculates a new value for the current EPAP setting for the valve 16 according to the formula $$Ea = Ea - \frac{\Delta E}{(Re + 1)}$$

where Ea is the current EPAP value, Re is an exhalation rounding factor of between 0 and 5, $\Delta E = Ea - Ep$ and Ep is the stored prescription EPAP level. It will be seen that if the exhalation rounding factor Re equals 0, then the leading edge when exhalation begins will immediately go to the prescribed EPAP level. If the rounding factor Re equals 1, each time a new current EPAP value is calculated, the curve will move closer to the prescribed EPAP level by one half of the deviation from the prescribed level. If the rounding factor Re equals 5, each time a new current EPAP value is calculated, the curve will move closer to the prescribed EPAP level by one sixth of the deviation from the prescribed level. At the block 52, the microprocessor 23 calculates the new value for the current IPAP according to the formula $$Ia = Ia + \frac{\Delta I}{(Ri + 1)}$$

where Ia is the current IPAP value, Ri is an inhalation rounding factor of between 0 and 5, $\Delta I = Ip - Ia$ and Ip is the stored prescription IPAP level.

It has been determined that a maximum rounding factor of 6 may be used if the cycle rate for updating the current EPAP and IPAP values is 16 Hz. and a maximum patient breathing rate is selected to be 24 breaths per minute. It would be rare for a sleeping patient to reach or exceed this breathing rate.

At this rate and if inhalation and exhalation times are equal, the patient would have 1.25 seconds each for inhalation and exhalation. By dividing the pressure deviation with a total rounding factor of 6, the current pressure will essentially reach the prescribed pressure prior to the changes between inhalation and exhalation at the fastest breathing rate. By dividing the pressure deviation with a total rounding factor of 1, the current pressure will immediately go to the prescribed pressure at changes between inhalation and exhalation. However, there is a risk that the person programming the inhalation and exhalation rounding factors into the apparatus 10 could mistakenly enter a value of zero. To avoid the possibility of division by zero, 1 is added to the rounding factor and the rounding factor is set to fall within the range of 0 to 5 rather than from 1 to 6.

It will be appreciated that various modifications and changes may be made to the above described preferred embodiment of a CPAP system without departing from the spirit and the scope of the following claims. In the preferred embodiment, separate rounding factors Re and Ri are provided for the EPAP transitions and the IPAP transitions. It should be appreciated that a single rounding factor may be used for both the EPAP and the IPAP transitions. Although the vent valve 16 is preferably located in a base unit with the blower 11, it should be appreciated that the vent valve may be located in or adjacent the mask 22. Alternately, the vent valve 16 may be eliminated and the pressure can be controlled by providing a fast response blower and controlling blower speed to provide the desired pressure waveform. The method used for producing a breathing signal is not a feature of the invention. Any of the various methods known in the art for generating a breathing signal which differentiates between inhalation and exhalation may be used.

I claim:

1. A continuous positive airway pressure system for respiratory therapy including a blower for establishing a flow of pressurized air, a hose adapted to deliver the pressurized air flow to a patient's respiratory system, means adapted to control the pressure of air delivered to the patient, and a controller adapted to control said pressure control means to establish a prescribed IPAP level during patient inhalation and a prescribed EPAP level during patient exhalation, the improvement comprising means for changing the profile of leading edges of the applied pressure waveform as such waveform alternately changes between EPAP and IPAP levels.

2. A continuous positive airway pressure system, as set forth in claim 1, and wherein said means for changing the profile of leading edges of the applied pressure waveform includes means for selectively providing a first adjustable shape to the leading edges of the waveform when said waveform changes from said EPAP level to said IPAP level, and means for selectively providing a second adjustable shape to the leading edges of the waveform when said waveform changes from said IPAP level to said EPAP level.

3. A continuous positive airway pressure system, as set forth in claim 2, and wherein said means for changing the profile of leading edges of the applied pressure waveform includes means for rounding the leading edges of said waveform.

4. A continuous positive airway pressure system, as set forth in claim 1, and wherein said means for changing the profile of leading edges of the applied pressure waveform includes means for selectively providing a predetermined adjustable shape to the leading edges of the waveform when said waveform changes both from said EPAP level to said IPAP level and from said IPAP level to said EPAP level.

5. In a bilevel continuous positive airway pressure system including a blower for establishing a flow of pressurized air, a hose adapted to deliver the pressurized air flow to a patient's respiratory system, a vent valve adapted to control the pressure of air delivered to the patient, and a controller adapted to control the vent valve to establish a prescribed IPAP level during patient inhalation and a prescribed EPAP level during patient exhalation, a method for controlling said vent valve comprising the step of:

a) establishing a control signal having a first level to establish said EPAP level and a second level to establish said IPAP level, said control signal having rounded leading edges when alternately changing between said first and second levels; and b) controlling said vent valve in response to said control signal.

6. A method for controlling a vent valve in a bilevel continuous positive airway pressure system, as set forth in claim 5, and wherein said control signal is established to control the profile of pressure transitions according to the formula $$Ia = Ia + \frac{\Delta I}{(Ri + 1)}$$

when changing from the EPAP level to the IPAP level and is established to control the profile of pressure transitions according to the formula $$Ea = Ea - \frac{\Delta E}{(Re + 1)}$$

when changing from the IPAP level to the EPAP level, where $\Delta I = Ip - Ia$, $\Delta E = Ea - Ep$, Ia is the actual inspiration pressure, Ip is the prescribed IPAP pressure, Ri an inspiration rounding factor, Ea is the actual expiration pressure, Ep is the prescribed EPAP pressure and Re is an expiration rounding factor.

* * * * *